US00PP26868P3

(12) United States Plant Patent
Olesen

(10) Patent No.: US PP26,868 P3
(45) Date of Patent: Jun. 28, 2016

(54) MINIATURE ROSE PLANT NAMED 'POULPAH073'

(50) Latin Name: ***Rosa* hybrid**
Varietal Denomination: Poulpah073

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 109 days.

(21) Appl. No.: 14/121,264

(22) Filed: Aug. 15, 2014

(65) Prior Publication Data

US 2016/0050807 P1 Feb. 18, 2016

(51) Int. Cl.
*A01H 5/00* (2006.01)

(52) U.S. Cl.
USPC ..... Plt./118

(58) Field of Classification Search
USPC ..... Plt./118
See application file for complete search history.

(56) References Cited

PUBLICATIONS

PLUTO Plant Variety Database Jan. 23, 2016 p. 1.*

* cited by examiner

*Primary Examiner* — Annette Para

(57) ABSTRACT

A new garden rose plant of the Miniature class which has abundant, yellow flowers and attractive foliage. This new and distinct variety has shown to be uniform and stable in the resulting generations from asexual propagation.

1 Drawing Sheet

Botanical designation: *Rosa* hybrid.
Variety denomination: 'Poulpah073'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpah073', originated as a single seedling from the stated cross.

The new variety may be distinguished from its male pollen parent and female seed parent by the following characteristics. The female seed parent has apricot flowers, while the new variety has yellow flowers. The male pollen parent has light yellow flowers, while the new variety has deep yellow flowers.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah073' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulpah073' was selected in the spring of 2007 by the inventor as a single plant from the progeny of the aforementioned hybridization.

Asexual reproduction of 'Poulpah073' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulpah073' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah073'. Specifically illustrated in the drawing are a flowering branch, flower in parts, flower buds, leaves, and stems. Plants shown are 2 years of age.

DETAILED DESCRIPTION OF THE VARIETY

The following is a description of 'Poulpah073', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulsun', U.S. Plant Pat. No. 9,716 dated Dec. 3, 1996, are compared to 'Poulpah073' in Chart 1.

CHART 1

| | 'Poulpah073' | 'Poulsun' |
|---|---|---|
| Petal Count | 25 | 30 to 35 |
| Flower Diameter | 60 mm | 50 to 63 mm |
| Upper petal colour | Yellow Group 12A | Yellow Group 13A |

FLOWER AND FLOWER BUD

Blooming habit: Continuous.

Flower bud:

*Size*.—Upon opening, 25 mm in length from base of receptacle to end of bud. Bud diameter is 10 mm.

*Bud form*.—Ovoid.

*Bud color*.—As sepals divide Yellow-Orange Group 14A with intonations of Orange-Red Group 32B.

*Sepal inner surface*.—Color: Yellow-Green Group 145B with Greyed-Orange Group 173B. Surface: Smooth.

*Sepal outer surface*.—Color: Yellow-Green Group 144A with Greyed-Red Group 182A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—25 mm long by 6 mm wide.

*Receptacle*.—Texture: Smooth. Size: 8 mm in height by 8 mm wide. Color: Yellow-Green Group 144A. Anthocyanic pigments the color of Greyed Group observed. Shape: Urn shaped.

*Pedicel*.—Surface: Smooth. Length: 7 mm. Diameter: 6 mm on average. Color: Yellow-Green Group 144A. Strength: Moderate.

Flower bud development: Flower buds are borne in clusters of 1 to 3 flower buds per stem.

Flower bloom:

*Fragrance*.—Moderate carnation like scent.

*Duration*.—The blooms have a duration on the plant of approximately 7 days. Petals fall cleanly away from plant after flowers have fully matured.

*Size*.—Flower diameter is 60 mm when open. Flower depth is 25 mm.

*Flower shape*.—General shape is an open cup with petals that curve out from the center.

*Shape of flower, side view*.—After opening, the upper portion is convex. The lower portion is concave.

Petalage: Under normal conditions, flowers have 25 petals.

General tonality of flower: Open flowers are Yellow Group 12A.

Petal color:

*Upon opening, outer and inner petals*.—Upper surface: Yellow Group 12A. Lower surface: Yellow Group 13B.

*Basal petal spots*.—None.

*After opening, outer petals*.—Upper surface: Yellow Group 12A. Lower surface: Yellow Group 13B.

*After opening, inner petals*.—Upper surface: Yellow Group 12A. Lower surface: Yellow Group 13B.

*Basal petal spots*.—None.

Petals:

*Petal reflex*.—Strong.

*Margin*.—Entire and uniform.

*Shape*.—Generally rounded. Apex shape: Rounded. Base shape: Rounded.

*Size*.—30 mm (l) by 26 mm (w).

*Texture*.—Smooth.

*Thickness*.—Average.

Reproductive organs:

*Pollen*.—None observed.

*Anthers*.—Size: 1 mm in length. Color: Yellow-Orange Group 18A. Quantity: 55 on average.

*Filaments*.—Color: Yellow-Green Group 13B. Length: 5 mm.

*Pistils*.—Length: 4 mm. Quantity: 20 on average.

*Stigmas*.—Color: Greyed-Yellow Group 160A.

*Styles*.—Color: Red-Purple Group N57A.

*Location of stigmas*.—Inferior in location relative to the length of the filaments and the height of the anthers.

*Hips*.—None Observed.

PLANT

Plant growth: Upright, bushy. Plants are 30 cm in height, and 30 cm wide.

Stems:

*Color*.—Juvenile growth: Yellow-Green Group 144B. Mature growth: Yellow-Green Group 144A.

*Length*.—On average, canes are 15 cm from the base of the plant to the flowering portion.

*Diameter*.—3 mm.

*Internodes*.—On mature canes, there is an average distance of 20 mm between nodes.

*Surface texture*.—Young wood: Smooth. Older wood: Smooth.

Long prickles: None.

Plant foliage:

*Compound leaf*.—75 mm (l)×35 (w).

*Quantity*.—4 leaves per 10 cm of stem on, average.

*Leaf bearing angle to the stem*.—45 degrees.

*Color of juvenile foliage*.—Upper side: Yellow-Green Group 144A. Margins are Greyed-Purple Group 183B. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 10 mm in length. 2 mm width. Quantity: 2 per compound leaf. Shape: Linear, slightly broad based with outward extending apices. Margins: Finely serrated. Color: Yellow-Green Group 145A.

*Petiole*.—Length: 20 mm. Diameter: 1 mm.

*Upper surface*.—Color: Yellow-Green Group 145B.

*Lower surface*.—Color: Yellow-Green Group 145A.

*Rachis*.—Length: 15 mm. Upper surface: Color: Yellow-Green Group 145B with some athocyanin in the Greyed-Purple Group 184A range.

*Lower surface*.—Color: Yellow-Green Group 145A. Observations: Small prickles.

*Leaflet*.—Quantity: Normal number of leaflets per leaf in middle of the stem is 5 leaflets. Margins: Serrated. Size: Average size of the terminal leaflet on normal leaves is 28 mm in length by 20 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora*

*sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpah073', substantially as illustrated and described herein, due to its abundant yellow flowers, disease resistance, and extended period of bloom.

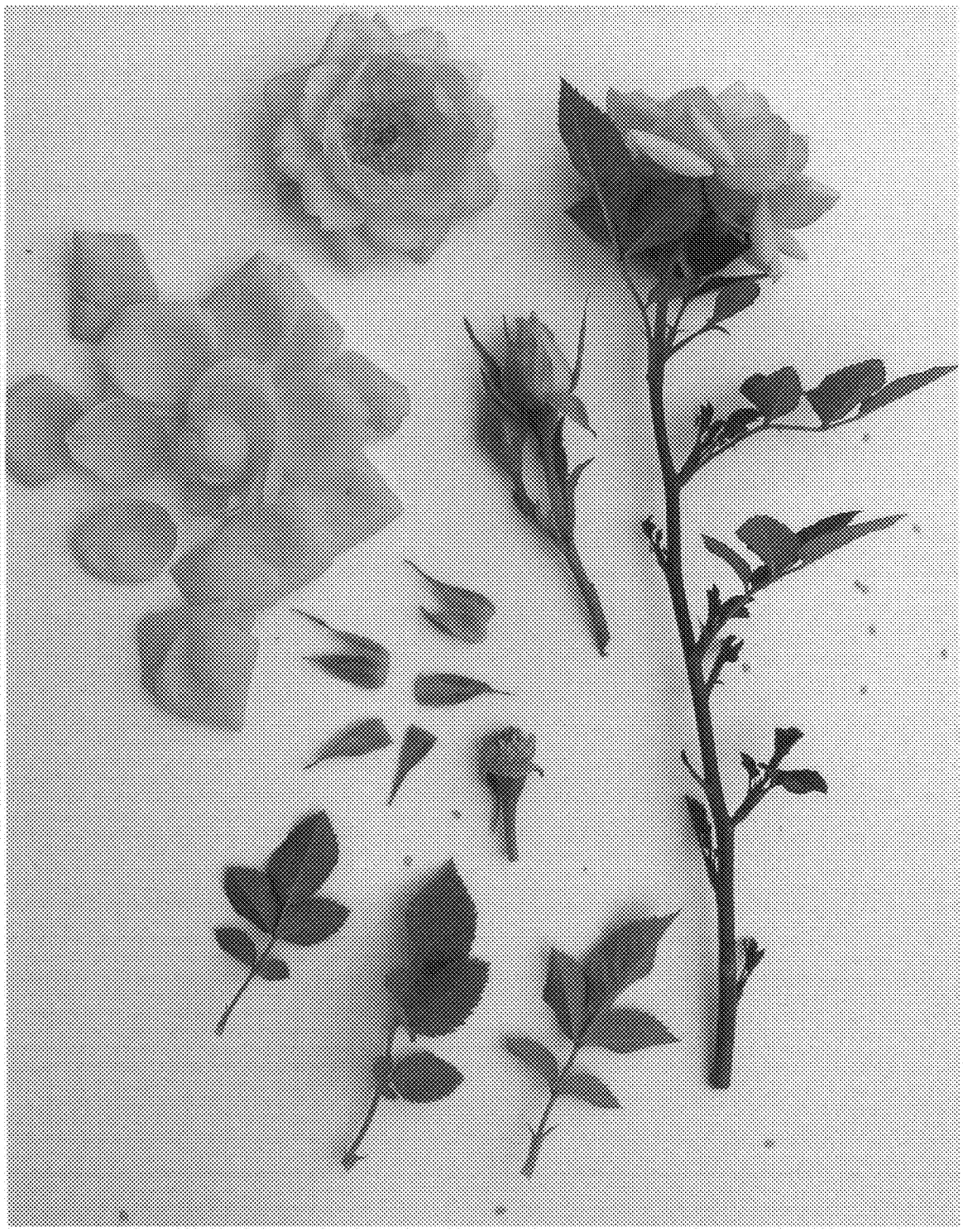

* * * * *